(12) United States Patent
Ruedinger et al.

(10) Patent No.: US 8,664,449 B2
(45) Date of Patent: Mar. 4, 2014

(54) METHOD FOR THE CONTINUOUS PRODUCTION OF 2-BUTANONE IN HOT PRESSURIZED WATER HAVING AN ADDED ELECTROLYTE

(75) Inventors: Christoph Ruedinger, Starnberg (DE); Hans-Juergen Eberle, Munich (DE); Andrea Soler, Darmstadt (DE); Herbert Vogel, Nauheim (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/820,260

(22) PCT Filed: Oct. 17, 2011

(86) PCT No.: PCT/EP2011/068115
§ 371 (c)(1),
(2), (4) Date: Mar. 1, 2013

(87) PCT Pub. No.: WO2012/052404
PCT Pub. Date: Apr. 26, 2012

(65) Prior Publication Data
US 2013/0197273 A1 Aug. 1, 2013

(30) Foreign Application Priority Data
Oct. 20, 2010 (DE) .......................... 10 2010 042 703

(51) Int. Cl.
*C07C 45/51* (2006.01)
(52) U.S. Cl.
USPC .......................................... 568/405

(58) Field of Classification Search
USPC .......................................... 568/405
See application file for complete search history.

(56) References Cited

PUBLICATIONS

Alexander et al., "Studies on the Mechanism of the Pinacol Rearrangement. I. Compounds Related to meso- and dl-2,3-Butanediol", J. Am Chem. Soc., vol. 73, pp. 1665-1668 (1951).
Bourns et al., "The Catalytic Action of Aluminum Silicates", Canadian Journal of Research, vol. 25, Sec. B, pp. 80-89 (1946).
Bucsi et al., "Transformation of 1,2-Diols over Perfluorinated Resinsulfonic Acids (Nafion-H)", Tetrahedron, vol. 50, No. 27, pp. 8195-8202 (1994).
Neish et al., "Production and Properties of 2,3-Butanediol", Canadian Journal of Research, vol. 23, Sec. B, pp. 281-289 (1945).
Ott et al., "Catalytic Dehydration of 1,2-Butanediol to n-Butyraldehyde in Sub- and Supercritical Water", Chem. Eng. Technol., vol. 28, No. 12, pp. 1561-1568 (2005).
Ott et al., "Influence of salts on the dehydration of several biomass-derived polyols in sub- and supercritical water", J. of Supercritical Fluids, vol. 38, pp. 80-93 (2006).
Sato et al., "Dehydration of diols catalyzed by CeO2", Journal of Molecular Catalysis A: Chemical, vol. 221, pp. 177-183 (2004).
International Search Report for PCT/EP2011/068115 dated Mar. 13, 2012.
International Preliminary Report of Patentability for PCT/EP2011/068115.

*Primary Examiner* — Sikarl Witherspoon
(74) *Attorney, Agent, or Firm* — Caesar, Rivise, Bernstein, Cohen & Pokotilow, Ltd.

(57) ABSTRACT

The invention relates to a method for continuously producing 2-butanone from 2,3-butanediol in hot pressurized water having an added electrolyte, characterized in that a compound selected from among the group comprising $Ce(SO_4)_2$, $Fe_2(SO_4)_3$, $Al_2(SO_4)$ is used as the added electrolyte.

13 Claims, 10 Drawing Sheets

(■ = 200 ppm (g g$^{-1}$) Al$_2$(SO$_4$)$_3$, ● = 270 ppm (g g$^{-1}$) Al$_2$(SO$_4$)$_3$,
▲ = 400 ppm (g g$^{-1}$) Al$_2$(SO$_4$)$_3$, □ = 800 ppm (g g$^{-1}$) Al$_2$(SO$_4$)$_3$,
△ = 1064 ppm (g g$^{-1}$) Al$_2$(SO$_4$)$_3$)

(■ = 200 ppm (g g$^{-1}$) Al$_2$(SO$_4$)$_3$, ● = 270 ppm (g g$^{-1}$) Al$_2$(SO$_4$)$_3$,
▲ = 400 ppm (g g$^{-1}$) Al2(SO4)3, □ = 800 ppm (g g$^{-1}$) Al$_2$(SO$_4$)$_3$,
△ = 1064 ppm (g g$^{-1}$) Al$_2$(SO$_4$)$_3$)

( ■ = without added salt, ● = 200 ppm (g g$^{-1}$) Fe$_2$(SO$_4$)$_3$,
▲ = 400 ppm (g g$^{-1}$) Fe$_2$(SO$_4$)$_3$, □ = 800 ppm (g g$^{-1}$) Fe$_2$(SO$_4$)$_3$)

(■ = without added salt, ● = 200 ppm (g g$^{-1}$) Fe$_2$(SO$_4$)$_3$, ▲ = 400 ppm (g g$^{-1}$) Fe$_2$(SO$_4$)$_3$, □ = 800 ppm (g g$^{-1}$) Fe$_2$(SO$_4$)$_3$)

(■ = without added salt, ● = 800 ppm (g g$^{-1}$) Ce(SO$_4$)$_2$,
▲ = 800 ppm (g g$^{-1}$) ZnSO$_4$ )

(■ = without added salt, ● = 800 ppm (g g$^{-1}$) Ce(SO$_4$)$_2$,
▲ = 800 ppm (g g$^{-1}$) ZnSO$_4$ )

($\blacksquare$ = 800 ppm (g g$^{-1}$) Ce(SO$_4$)$_2$, $\bullet$= 200 ppm (g g$^{-1}$) Al$_2$(SO$_4$)$_3$, $\blacktriangle$ = 200 ppm (g g$^{-1}$) Fe$_2$(SO$_4$)$_3$, $\square$= 800 ppm ZnSO$_4$ (g g$^{-1}$))

(■ = 800 ppm (g g$^{-1}$) Ce(SO$_4$)$_2$, ● = 200 ppm (g g$^{-1}$) Al$_2$(SO$_4$)$_3$, ▲ = 200 ppm (g g$^{-1}$) Fe$_2$(SO$_4$)$_3$, □ = 800 ppm ZnSO$_4$ (g g$^{-1}$))

(■ = 800 ppm (g g$^{-1}$) Ce(SO$_4$)$_2$, ● = 200 ppm (g g$^{-1}$) Al$_2$(SO$_4$)$_3$, ▲ = 200 ppm (g g$^{-1}$) Fe$_2$(SO$_4$)$_3$, □ = 800 ppm ZnSO$_4$ (g g$^{-1}$))

METHOD FOR THE CONTINUOUS PRODUCTION OF 2-BUTANONE IN HOT PRESSURIZED WATER HAVING AN ADDED ELECTROLYTE

BACKGROUND OF THE INVENTION

The invention relates to a method for continuously producing 2-butanone from 2,3-butanediol in hot pressurized water having an added electrolyte.

2-Butanone is primarily used as a fuel additive and as a solvent for varnishes, plastics, resins, nitrocellulose and acetyl cellulose. In addition, it is also used for deparaffinization of lubricating oils. A considerably lower proportion of 2-butanone is used as a starting material for preparing methyl isopropenyl ketone and methyl and ethyl amyl ketone. In the presence of hydrogen peroxide, methyl ethyl ketone is converted to methyl ethyl ketone peroxide, a polymerization initiator.

The reaction of polyols having hydroxyl groups in the 1,4-positions, such as 1,4-butanediol, gives rise to the corresponding tetrahydrofuran derivatives. In contrast, the dehydration of diols having neighbouring hydroxyl groups, for example 1,2-propanediol and 1,2-butanediol, yields the corresponding aldehyde or ketone.

The dehydration of 2,3-butanediol has previously been carried out by means of heterogeneous and homogeneous catalysis. Aluminosilicates (A. N. Bourns, R. V. V. Nicholls, *Can. J. Res. B* 1946-1947, 24-25, 80 ff) and Nafion®-H (I. Bucsi, A. Molnár, M. Bartók, *Tetrahedron* 1994, 50, 27, 8195 ff) were used as heterogeneous catalysts. Sulfuric acid (A. C. Neish, V. C. Haskell, F. J. MacDonald, *Can. J. Res. B* 1945, 23, 281 ff) or phosphoric acid (E. R. Alexander, D. C. Dittmer, *J. Am. Chem. Soc.* 1951, 73, 1665 ff) were used for homogeneously catalysed dehydration. In all experiments, 2-butanone and isobutyraldehyde, and also its acetal with 2,3-butanediol, were obtained in varying proportions. Bourns was able to obtain 2-butanone in 85% yield in a gas phase reaction at 225° C. over aluminosilicate. The yield declined at higher temperatures, while above 450° C. only gaseous decomposition products were formed. Bucsi likewise achieved a selectivity for 2-butanone of 83% with almost complete conversion, by heterogeneous catalysis over Nafion®-H catalysts, while the formation of isobutyraldehyde could be almost completely eliminated (S=3%). Neish investigated the kinetics of dehydration to 2-butanone with addition of 3-20% (g g$^{-1}$) sulfuric acid. For the rac-meso starting materials (isomeric mixture of (R,R)- and (S,S)- and meso-2,3-butanediol), distillation with 85% phosphoric acid results in a combined yield of 2-butanone and isobutyraldehyde of 59%. The use of high acid concentrations, however, is accompanied by increased corrosion of the reactor. Furthermore, an additional neutralization is required during workup.

It is also known that, by addition of zinc sulfate and nickel sulfate in subcritical and supercritical water, the conversion of polyols and also the yield can be increased. On dehydration of meso-erythritol to the major product 1,4-anhydroerythritol in water, the maximum yield is 55% at 360° C., 340 bar and with 988 ppm (g g$^{-1}$) zinc sulfate. Starting from 1,2-propanediol in sub- and supercritical water, the maximum yield of propionaldehyde achieved is 90% at 360° C., 340 bar, residence time 120 s and with 400 ppm (g g$^{-1}$) zinc sulfate. At 320° C., 34 MPa and a residence time of 90 s, the conversion is approx. 70% and the yield is 70% (L. Ott, S. Kohl, M. Bicker, H. Vogel, *Chem. Eng. Technol.* 2005, 28, 1561). On conversion of 1,2-butanediol to n-butyraldehyde in the presence of 400 ppm (g g$^{-1}$) zinc sulfate at 340° C. and 340 bar, a maximum yield of 70% is achieved after a residence time of 120 s (L. Ott, V. Lehr, S. Urfels, M. Bicker, H. Vogel, *J. Supercrit. Fluids* 2006, 38, 80 ff). This reaction procedure is unfavourable since zinc sulfate is very expensive and nickel sulfate is classified as environmentally harmful according to the hazardous substance regulations.

The object of the invention is to provide a method which optimizes the continuous production of 2-butanone from 2,3-butanediol in hot pressurized water having an added electrolyte.

DESCRIPTION OF THE INVENTION

The object is achieved by a method in which a mixture comprising 2,3-butanediol in hot pressurized water is converted to 2-butanone, characterized in that a compound selected from the group comprising $Ce(SO_4)_2$, $Fe_2(SO_4)_3$, $Al_2(SO_4)_3$ is used as the added electrolyte.

The added electrolyte is preferably used at a concentration of 200-1100 ppm (g g$^{-1}$), iron sulfate preferably being used at a concentration of 200-800 ppm (g g$^{-1}$) (0.5-2 mmol L$^{-1}$), particularly preferably at 200 ppm (g g$^{-1}$) (0.5 mmol L$^{-1}$), aluminum sulfate preferably being used at a concentration of 200-1064 ppm (g g$^{-1}$) (0.58-3.11 mmol L$^{-1}$), particularly preferably 200 ppm (g g$^{-1}$) (0.58 mmol L$^{-1}$), and cerium sulfate preferably being used at a concentration of 800 ppm (g g$^{-1}$) (2.41 mmol L$^1$). The reaction with iron sulfate and aluminum sulfate takes place, owing to the hydroxide formation, preferably in a solution having a pH<7, particularly preferably a 5% (g g$^{-1}$) acetic acid solution, while cerium sulfate is preferably used as a solution in water.

In the method according to the invention, preferably a solution of 0.5-20% (g g$^{-1}$) or 0.056-2.22 mol L$^{-1}$ of 2,3-butanediol in water is used as reactant. 2,3-Butanediol occurs as three stereoisomers, which can be biochemically isolated from each other; the two enantiomers (R,R)- and (S,S)-2,3-butanediol as well as a meso form (R,S)-2,3-butanediol. In the process according to the invention, preference is given to using an isomer mixture of (R,R)- and (S,S)-2,3-butanediol, and also the meso form (R,S)-2,3-butanediol, which is also referred to in the application as rac-meso-2,3-butanediol.

The reaction is conducted under conditions under which hot pressurized water is present. These preferably involve a temperature of 300° C. to 400° C., particularly preferably 320° C., and a pressure of preferably 300 to 400 bar, particularly preferably 340 bar.

The reaction time (hydrodynamic residence time in the reaction chamber) is preferably 5-200 s. A dehydration of 2,3-butanediol in sub- and supercritical water (high-pressure water) is advantageous since a biochemically produced dilute aqueous butanediol solution can be converted to 2-butanone, without prior removal of water, directly in a high-pressure apparatus. The reaction in sub- and supercritical water is particularly advantageous, since no additional neutralization is required during workup.

The use of iron sulfate and aluminum sulfate is advantageous as these salts are very inexpensive. Aluminum sulfate and similarly iron sulfate are environmentally friendly, according to the hazardous substance regulations, in comparison with zinc sulfate and nickel sulfate.

By the addition of aluminum sulfate, iron sulfate and cerium sulfate, according to the invention, the same yields of up to 70 mol % of 2-butanone can be obtained as with zinc sulfate. This can be seen in FIGS. 9 and 10. The enhanced activity of iron sulfate and aluminum sulfate is apparent from FIG. 8. The yields of isobutyraldehyde also correspond to those with addition of zinc sulfate. It was apparent, however, that Ce(SO$_4$)$_2$, Fe$_2$(SO$_4$)$_3$, and/or Al$_2$(SO$_4$)$_3$ have an enhanced activity, in comparison with zinc sulfate or nickel sulfate, for the conversion of 2,3-butanediol to 2-butanone, and therefore allow better space-time yields than zinc sulfate or nickel sulfate.

The following examples serve to further illustrate the invention.

Figure 1:
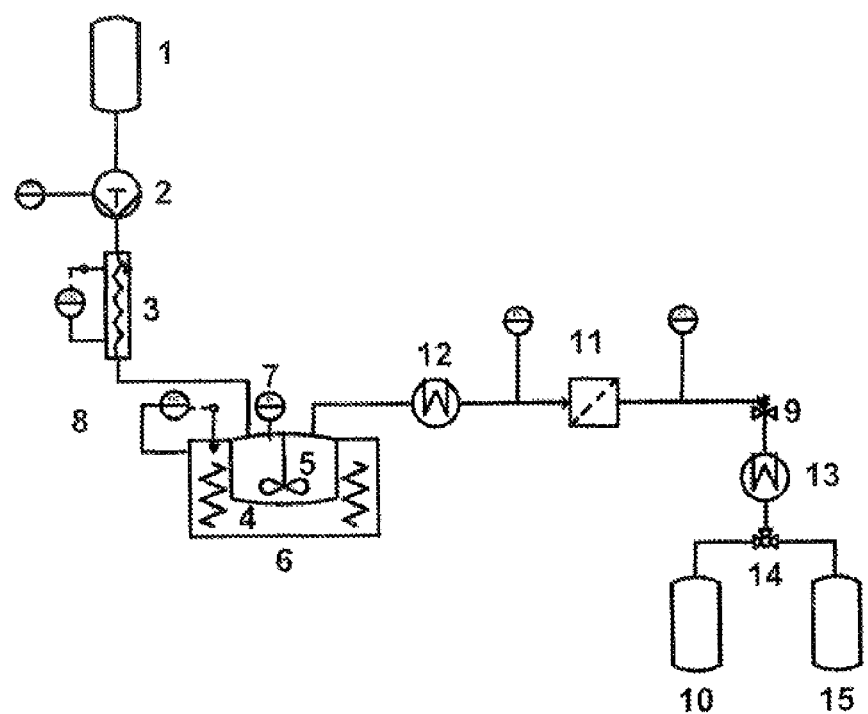
FIG. 1 shows a flow diagram of the apparatus used in the examples.

The experiments were carried out in an apparatus shown in FIG. 1 and described in the following:

By means of HPLC pumps (Kontron®, pump head 10 mL) (1), the homogeneous reaction solution was conveyed from a reservoir (2) into the pre-heater (3) and then into the reactor (4). A flow tube reactor having a volume of 2.2 cm$^3$ (stainless steel, materials number 1.4571) served as pre-heater (3), which was operated at 150° C. It was established in preliminary experiments that no reaction takes place at this temperature. The reactor unit (4) consisted of an electrically heated continuous stirred tank reactor (5) (Inconel®625, materials number 2.4856), which was set into an aluminum block (6). This was electrically heated by means of 5 heating elements each of 400 W; temperature regulation was effected by a regulator having two thermocouples (7, 8), one of which (7) measured the temperature of the solution in the reactor. A second thermocouple (8) was located in the outer aluminum block (6). The volume of the stirred tank reactor (4) was 5 cm$^3$. The reaction solution was then cooled to 7° C. in a heat exchanger and depressurized to atmospheric pressure via a pressure release valve (9). The product mixture was then collected in a cooled sample vessel (10). In order to remove potential solid reaction products, a filter (11) (90 μm) was situated after the heat exchanger (stainless steel, materials number 1.4571).

This resulted in a residence time window in the reactor (4), adjustable via the pump (1) flow rate, of 15 to 180 seconds.

The sample obtained from the reactor (4) was mixed with an ion exchanger (Amberlite IR120H$^+$ form). This pre-treatment with an ion exchanger was intended to bind heavy metal ions leached from the stainless steel and protect the HPLC column from contamination. The quantitative analysis was carried out by HPLC on an ion exchange column (ION-300H, Interaction Chromatography, Inc.).

EXAMPLE 1

An aqueous solution consisting of 0.5% (g g$^{-1}$) rac-meso-2,3-butanediol and 200-1064 ppm (g g$^{-1}$) aluminum sulfate (0.58-3.11 mmol L) in 5% (g g$^{-1}$) acetic acid solution was reacted as described above at 320° C. and 34 MPa. 2-Butanone as the main product and isobutyraldehyde as the by-product were identified and quantified by HPLC. At a residence time of 120 s, 34 MPa and 320° C. without added electrolyte, a conversion of 2 mol % was achieved.

Figure 2:
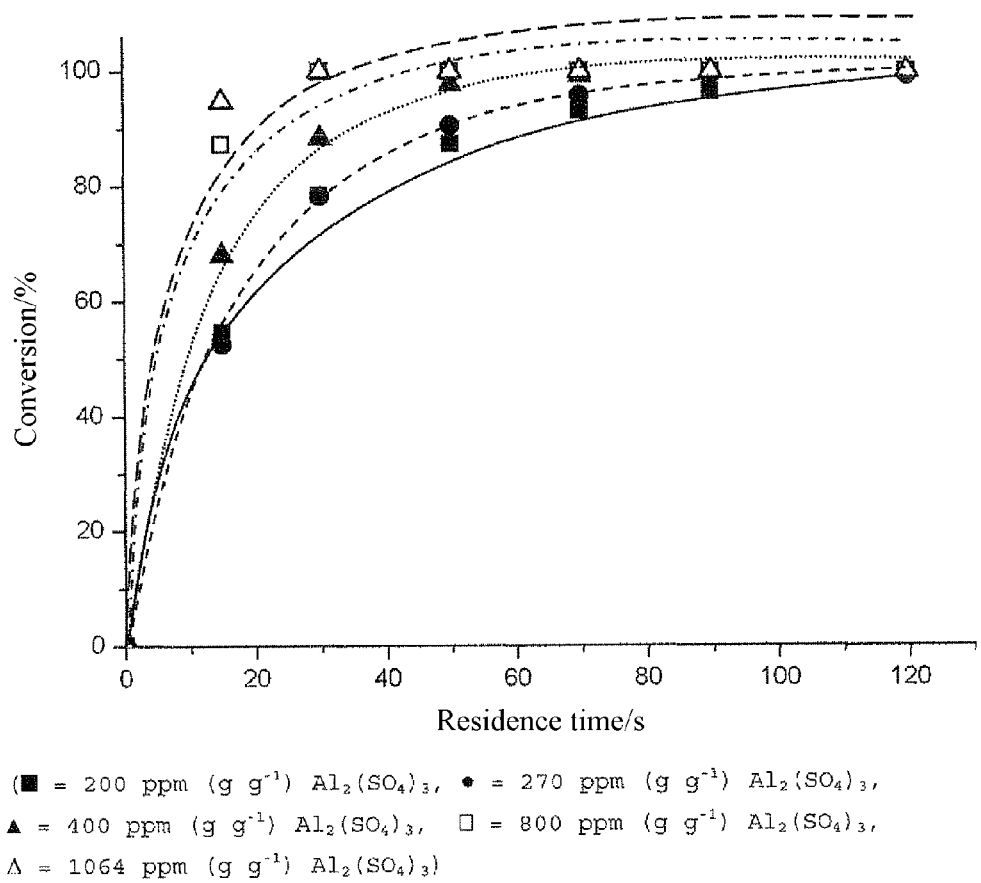
FIG. 2 shows the conversion of 2,3-butanediol, as a function of the residence time, with addition of 200-1064 ppm (g g$^{-1}$) Al$_2$(SO$_4$)$_3$ at 320° C. and 34 MPa, from example 1.

The conversion after 120 s at 320° C. was complete on addition of aluminum sulfate (0.58 mmol L$^{-1}$=approx. 200 ppm (g g$^{-1}$) Al$_2$(SO$_4$)$_3$). Even after a residence time of 15 s, a conversion amounting to 55 mol % was reached. FIG. 2 shows these results from example 1 (conversion of 2,3-butanediol with Al$_2$(SO$_4$)$_3$ as added electrolyte at 320° C. as a function of residence time).

Figure 3:
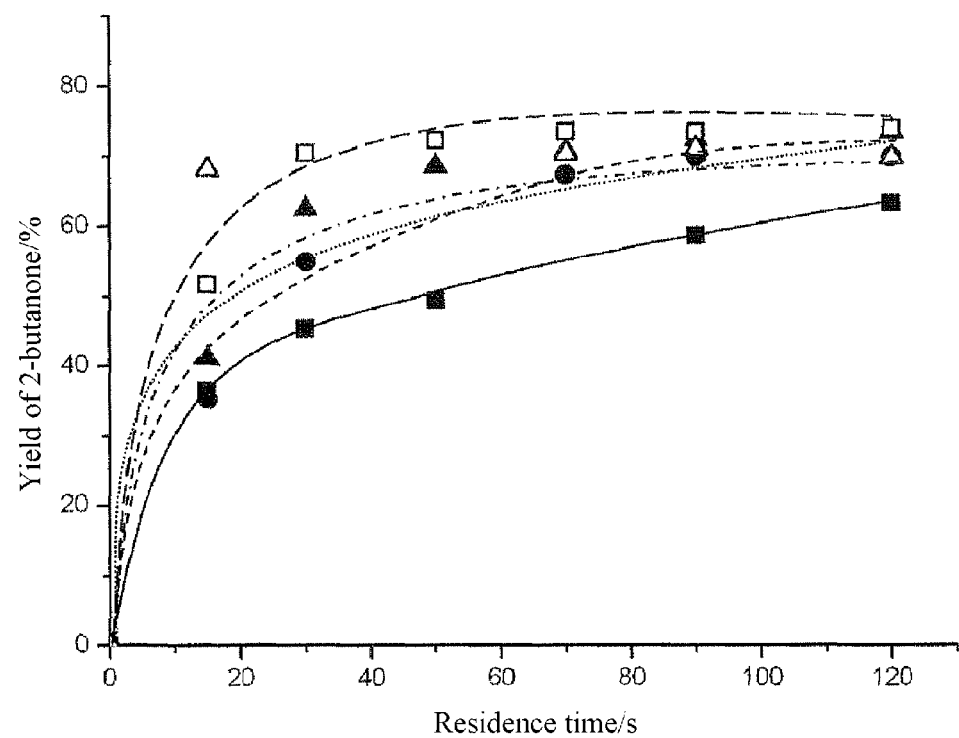
FIG. 3 shows the yield of 2-butanone, as a function of the residence time, with addition of 200-1064 ppm (g g$^{-1}$) Al$_2$(SO$_4$)$_3$ at 320° C. and 34 MPa, from example 1.

The maximum yield of the desired main product 2-butanone was approx. 70 mol % at 320° C. with addition of 270 ppm (g g$^{-1}$) aluminum sulfate. The maximum selectivity with respect to 2-butanone at 360° C. with added salt was 70 mol %. FIG. 3 shows these results from example 1 (yield of 2-butanone with Al$_2$(SO$_4$)$_3$ as added electrolyte at 320° C. as a function of residence time).

EXAMPLE 2

Figure 4:
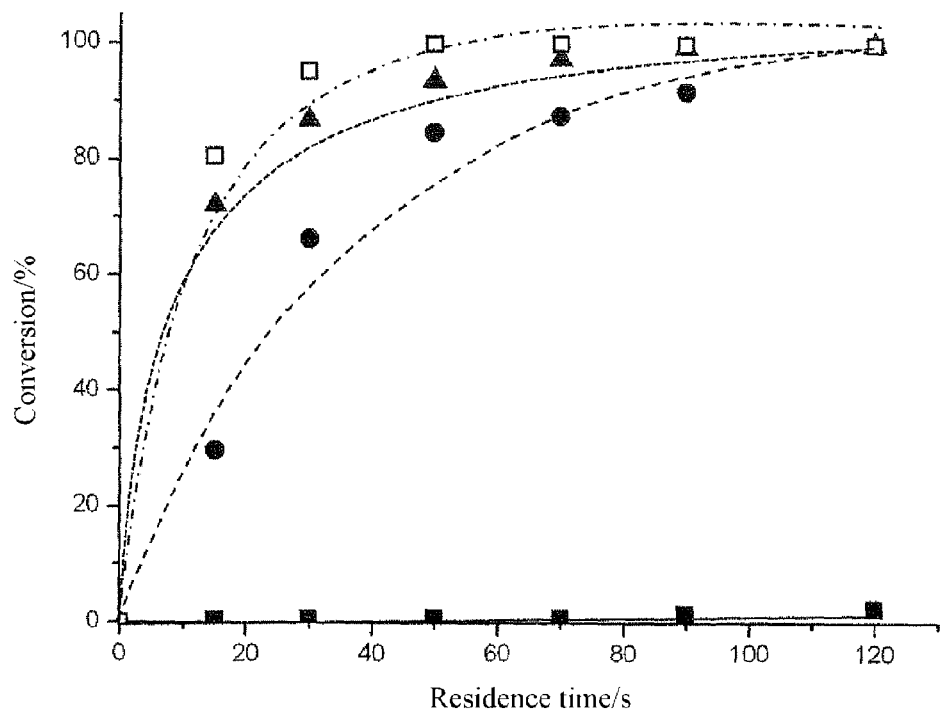
FIG. 4 shows the conversion of rac-meso-2,3-butanediol as a function of the residence time, without and with addition of 200-800 ppm (g g$^{-1}$) Fe$_2$(SO$_4$)$_3$ at 320° C. and 34 MPa, from example 2.

The reaction was conducted analogously to example 1. Rac-meso-2,3-butanediol was used as reactant in 5% (g g$^{-1}$) aqueous acetic acid solution. The reaction took place at 320° C., 34 MPa and with addition of 200-800 ppm (g g$^{-1}$) iron sulfate (0.5-2.00 mmol L$^{-1}$). By addition of iron sulfate at 320° C., the conversion could be considerably enhanced. In the case of addition of 400 and 800 ppm (g g$^{-1}$) Fe$_2$(SO$_4$)$_3$, complete conversion was achieved at a residence time of 120 s. FIG. 4 shows these results from example 2 (conversion of reactant as a function of residence time).

Figure 5:
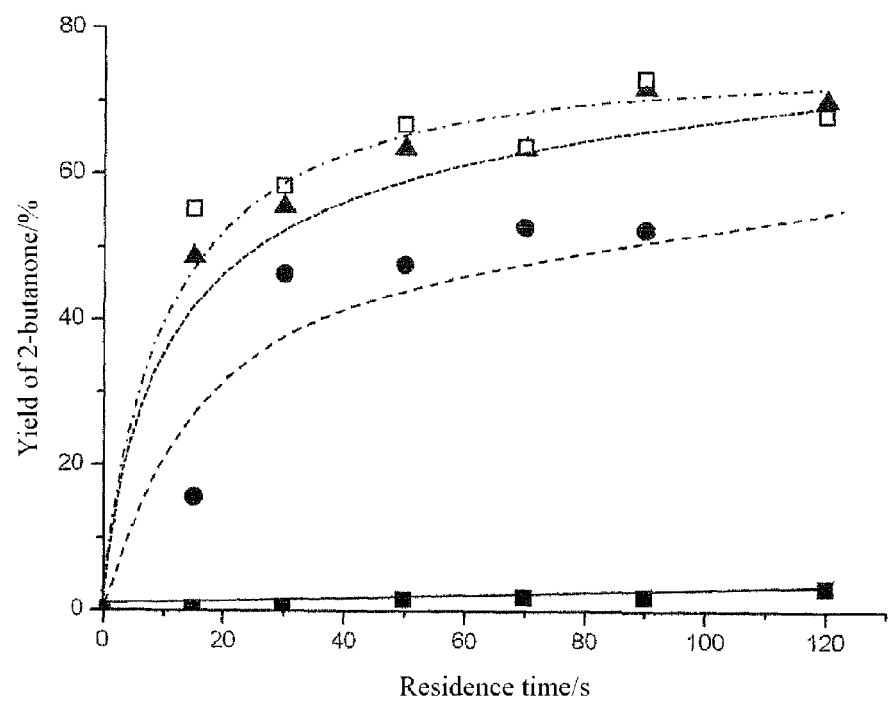
FIG. 5 shows the yield of 2-butanone, as a function of the residence time, without and with addition of 200-800 ppm (g g$^{-1}$) Fe$_2$(SO$_4$)$_3$ at 320° C. and 34 MPa, from example 2.

The yield of 2-butanone could be increased from 3 to 21 mol % by addition of 200 ppm (g g$^{-1}$) (0.5 mmol L$^{-1}$) Fe$_2$(SO$_4$)$_3$. A maximum yield of 70 mol % was achieved by addition of 800 ppm (g g$^{-1}$) (2 mmol L$^{-1}$) Fe$_2$(SO$_4$)$_3$ at a residence time of 90 s. These results are depicted in FIG. 5.

EXAMPLE 3

Figure 6:
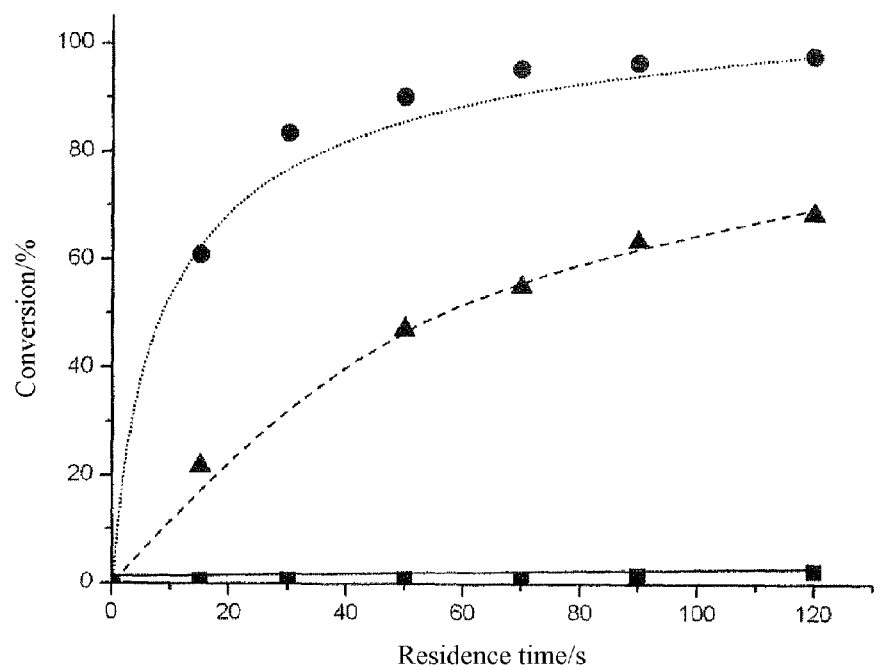
FIG. 6 shows the conversion of 2,3-butanediol, as a function of residence time, with and without addition of salt at 320° C. and 34 MPa, from example 3.
Figure 7:
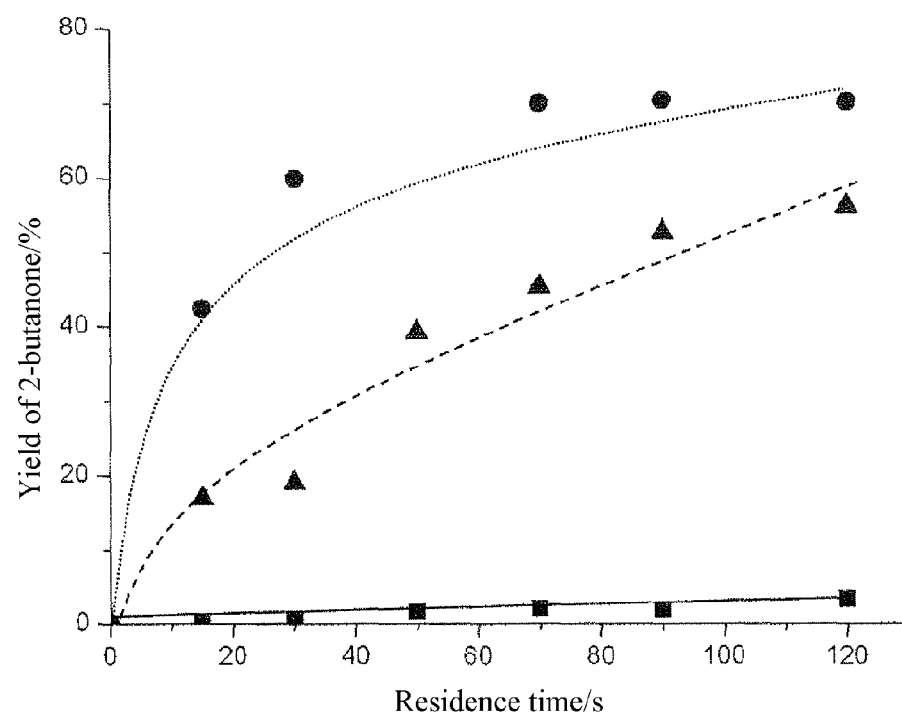
FIG. 7 shows the yield of 2-butanone, as a function of residence time, with and without addition of salt at 320° C. and 34 MPa, from example 3.

The reaction was conducted according to example 1. Rac-meso-2,3-butanediol was used as reactant. The reaction took place at 320° C., 34 MPa and with addition of 800 ppm (g g$^{-1}$) cerium sulfate (2.41 mmol L$^{-1}$). For comparison, the analogous reaction with addition of zinc sulfate was carried out. The results obtained are depicted in FIGS. 6 and 7. By addition of cerium sulfate, a higher conversion was achieved than with zinc sulfate under the same reaction conditions. Maximum conversion of 98 mol % was achieved at a residence time of 120 s. At a residence time of 120 s, the maximum yield with respect to 2-butanone is 70 mol %.

EXAMPLE 4

Figure 8:
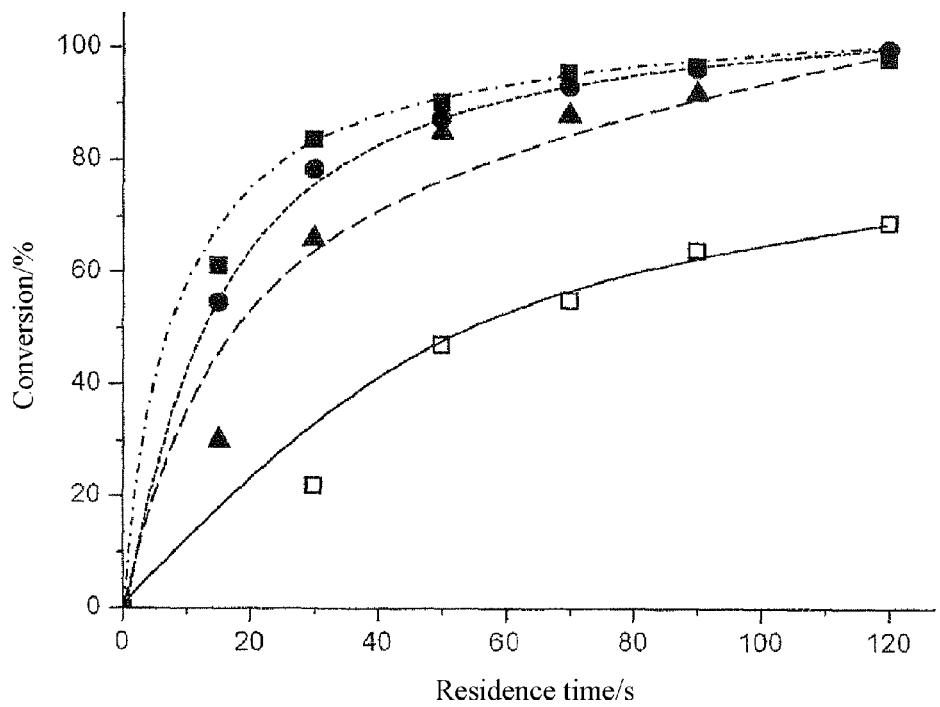
FIG. 8 shows the conversion of rac-meso-2,3-butanediol at 320° C. and 340 bar, as a function of residence time, with addition of 200 ppm (g g$^{-1}$) Al$_2$(SO$_4$)$_3$, 200 ppm (g g$^{-1}$) Fe$_2$(SO$_4$)$_3$, 800 ppm (g g$^{-1}$) Ce(SO$_4$)$_2$ and 800 ppm (g g$^{-1}$) ZnSO$_4$, from example 4.
Figure 9:
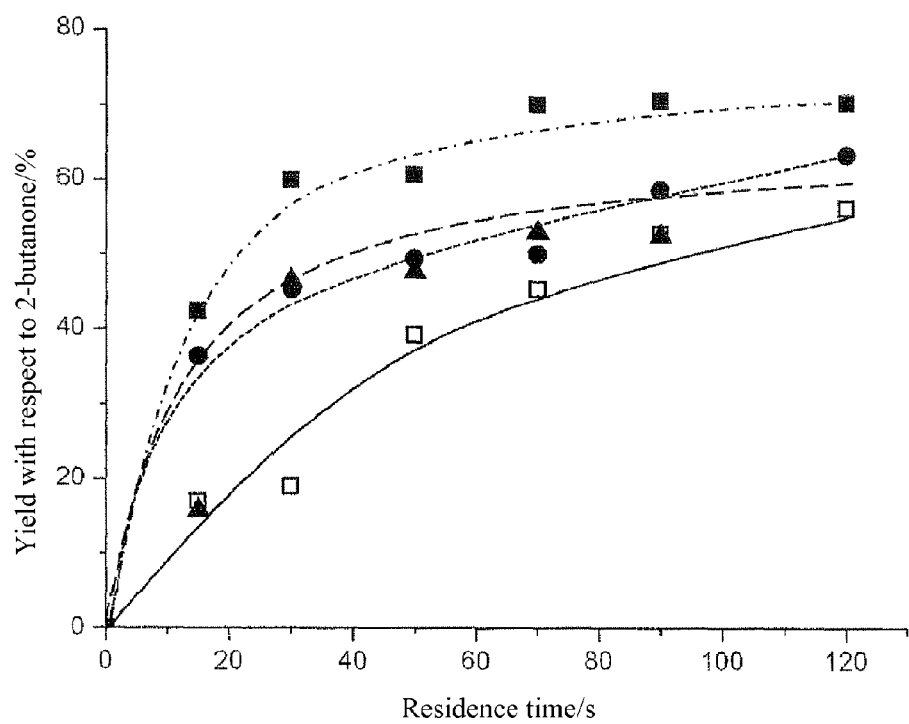
FIG. 9 shows the yield with respect to 2-butanone at 320° C. and 340 bar, as a function of the residence time, with addition of 200 ppm (g g$^{31}$) Al$_2$(SO$_4$)$_3$, 200 ppm (g g$^{-1}$) Fe2(SO$_4$)$_3$, 800 ppm (g g$^{-1}$) Ce(SO$_4$)$_2$ and 800 ppm (g g$^{-1}$) ZnSO$_4$, from example 4.
Figure 10:
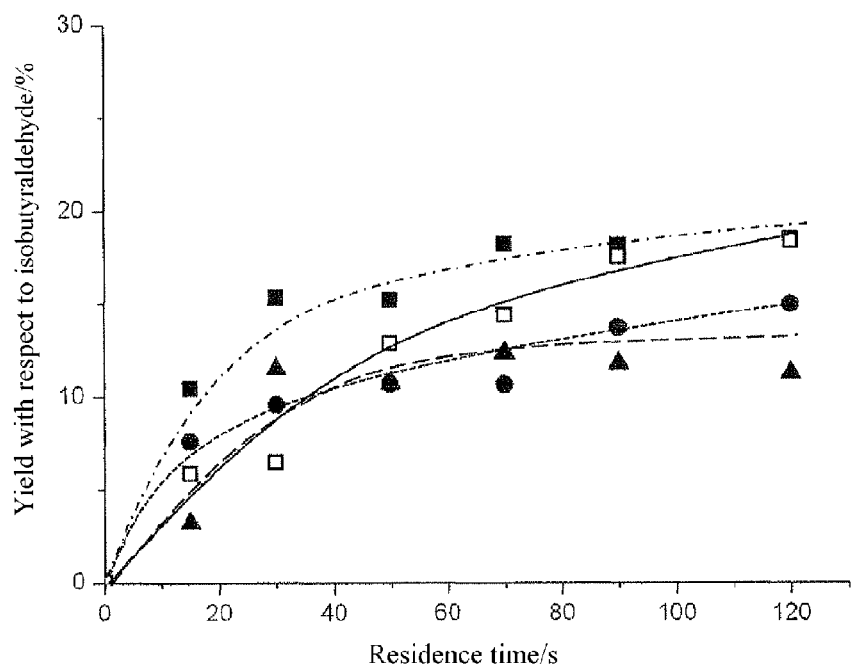
FIG. 10 shows the yield with respect to isobutyraldehyde at 320° C. and 340 bar, as a function of the residence time, with addition of 200 ppm (g g$^{31\ 1}$) Al$_2$(SO$_4$)$_3$, 200 ppm (g g$^{-1}$) Fe$_2$(SO$_4$)$_3$, 800 ppm (g g$^{-1}$) Ce(SO$_4$)$_2$ and 800 ppm (g g$^{-1}$) ZnSO$_4$, from example 4.

The reaction was conducted according to example 1. For the reaction with addition of aluminum sulfate or iron sulfate, an aqueous solution consisting of 0.5% (g g$^{-1}$) rac-meso-2,3-butanediol and 200 ppm (g g$^{-1}$) aluminum sulfate or iron sulfate (0.58 and 0.5 mmol L$^{-1}$ respectively) in 5% (g g$^{-1}$) acetic acid solution was used. As a further addition, 800 ppm (g g$^{-1}$) cerium sulfate were used in an aqueous solution consisting of 0.5% (g g$^{-1}$) rac-meso-2,3-butanediol. The reaction took place at 320° C., 34 MPa and with the addition of the corresponding electrolyte. For comparison, the analogous reaction with addition of zinc sulfate was carried out. The results obtained are depicted in FIGS. 8-10. By addition of aluminum sulfate, iron sulfate or cerium sulfate, a higher conversion was achieved than with zinc sulfate under the same reaction conditions. Maximum conversion of 100 mol % was achieved at a residence time of 120 s by addition of 200 ppm (g g$^{-1}$) iron sulfate. At a residence time of 120 s, the maximum yield with respect to 2-butanone was 70 mol % after

The invention claimed is:

1. A method for continuously producing 2-butanone, said method comprising conducting a dehydration reaction of 2,3-butanediol in hot pressurized water having an added electrolyte, wherein the reaction is conducted at a temperature of 300° C. to 400° C., and a pressure of 300 to 400 bar, and the added electrolyte is at least one compound selected from the group consisting of $Ce(SO_4)_2$, $Fe_2(SO_4)_3$, and $Al_2(SO_4)_3$.

2. The method as claimed in claim 1, wherein the added electrolyte is used at a concentration of 200-1100 ppm (g g$^{-1}$).

3. The method as claimed in claim 1, wherein a solution of 0.5-20% (g g$^{-1}$) or 0.056-2.22 mol L$^{-1}$ of 2,3-butanediol in water is used as reactant.

4. The method as claimed in claim 1, wherein the temperature at which the reaction is conducted is 320° C., and the pressure at which the reaction is conducted is 340 bar.

5. The method as claimed in claim 1, wherein the reaction is conducted in a reaction chamber with a hydrodynamic residence time in the reaction chamber of 5 to 200 s.

6. The method as claimed in claim 2, wherein a solution of 0.5-20% (g g$^{-1}$) or 0.056-2.22 mol L$^{-1}$ of 2,3-butanediol in water is used as reactant.

7. The method as claimed in claim 2, wherein the reaction is conducted at a temperature of 320° C., and a pressure of 340 bar.

8. The method as claimed in claim 3, wherein the reaction is conducted at a temperature of 320° C., and a pressure of 340 bar.

9. The method as claimed in claim 2, wherein the reaction is conducted in a reaction chamber with a hydrodynamic residence time in the reaction chamber of 5 to 200 s.

10. The method as claimed in claim 3, wherein the reaction is conducted in a reaction chamber with a hydrodynamic residence time in the reaction chamber of 5 to 200 s.

11. The method as claimed in claim 4, wherein the reaction is conducted in a reaction chamber with a hydrodynamic residence time in the reaction chamber of 5 to 200 s.

12. The method as claimed in claim 11, wherein the added electrolyte is used at a concentration of 200-1100 ppm (g g$^{-1}$).

13. The method as claimed in claim 12, wherein a solution of 0.5-20% (g g$^{-1}$) or 0.056-2.22 mol L$^{-1}$ of 2,3-butanediol in water is used as reactant.

\* \* \* \* \*